United States Patent
Alanen et al.

(10) Patent No.: US 6,762,609 B2
(45) Date of Patent: Jul. 13, 2004

(54) METHOD FOR MEASURING SKIN SURFACE HYDRATION AND DEVICE FOR APPLYING THE METHOD

(75) Inventors: Esko Alanen, Kuopio (FI); Aulis Tapani Lahtinen, Kuopio (FI); Jouni Nuutinen, Kuopio (FI)

(73) Assignee: Delfin Technologies LTD, Kuopio (FI)

( * ) Notice: Subject to any disclaimer, the term of this patent is extended or adjusted under 35 U.S.C. 154(b) by 85 days.

(21) Appl. No.: 10/144,357

(22) Filed: May 14, 2002

(65) Prior Publication Data

US 2003/0214311 A1 Nov. 20, 2003

Related U.S. Application Data

(63) Continuation of application No. PCT/FI00/01001, filed on Nov. 16, 2000.

(30) Foreign Application Priority Data

Nov. 16, 1999 (FI) .................................................. 992455

(51) Int. Cl.[7] .......................... G01R 27/26; A51B 5/053
(52) U.S. Cl. ....................... 324/686; 324/689; 324/690; 600/547
(58) Field of Search ................................ 324/686, 665, 324/689, 690; 600/547

(56) References Cited

U.S. PATENT DOCUMENTS

| | | | | |
|---|---|---|---|---|
| 4,777,599 A | * | 10/1988 | Dorogi et al. | 600/552 |
| 4,860,753 A | * | 8/1989 | Amerena | 324/690 |
| 4,966,158 A | * | 10/1990 | Honma et al. | 324/689 |
| 5,086,279 A | | 2/1992 | Wochnowski et al. | 324/637 |
| 5,459,403 A | | 10/1995 | Kohler et al. | 324/643 |
| 5,588,440 A | * | 12/1996 | Cowie | 600/547 |
| 6,370,426 B1 | * | 4/2002 | Campbell et al. | 324/696 |
| 6,469,524 B1 | * | 10/2002 | Oberdier | 324/688 |

FOREIGN PATENT DOCUMENTS

| | | |
|---|---|---|
| DE | 34 33 192 | 4/1985 |
| DE | 196 52 679 | 4/1998 |
| GB | 2 148 513 | 5/1985 |
| GB | 2 194 340 | 3/1988 |
| GB | 2 293 017 | 3/1996 |

* cited by examiner

Primary Examiner—N. Le
Assistant Examiner—Timothy J. Dole
(74) Attorney, Agent, or Firm—Pillsbury Winthrop LLP

(57) ABSTRACT

A method for measuring the moisture content of skin, includes placing a probe on the skin for measuring the capacitance of the skin. An apparatus for applying the method, includes a probe and devices connected to the probe for transmitting, transferring and analyzing a signal. A wave signal is transmitted into the probe, the capacitance of the probe is measured by comparing the wave phases of the transmitted and reflected waves, and the applied radio frequency is low, approximately 0.2 to 5 MHz. The apparatus also includes a device into which a wave formed by the signal reflected from the probe is arranged to be led into a first input; and into which a wave forming the signal and transmitted to the probe is arranged to be led into a second input, whereat the capacitance can be measured by comparing the wave phases.

11 Claims, 3 Drawing Sheets

METHOD FOR MEASURING SKIN SURFACE HYDRATION AND DEVICE FOR APPLYING THE METHOD

Figure 1:
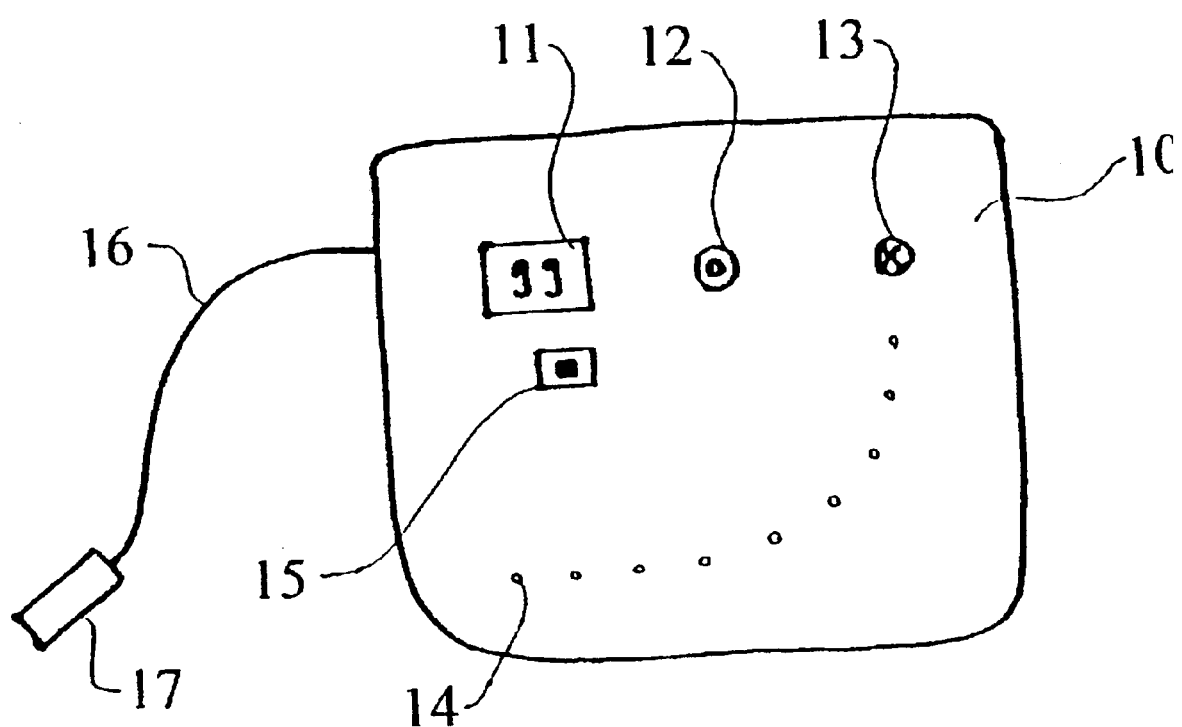

This application is a continuation of PCT/FI00/01001, filed Nov. 16, 2000, which designated the United States.

The present invention relates to a method for measuring the moisture content of skin, in which method a probe is placed on the skin for measuring the capacitance of the skin. The invention relates also to the apparatus for applying the method, which apparatus comprises a probe to be placed on the skin and devices connected to the probe for transmitting and transferring a signal into the probe and back from the probe in order to transfer and analyse the reflected signal and for measuring the capacitance of the skin.

The skin consists of three layers, which are, from the surface inwards, stratum corneum, epidermis and dermis. The water content is low in the stratum corneum and high in the dermis. The water content increases gradually from the surface of epidermis to deeper parts of epidermis. The hydration of skin is determined by the properties of the stratum corneum. Dry skin feels rough and will become wrinkled faster than normal skin. People living in dry weather conditions suffer from dry skin more than others and have to apply cosmetic products for moisturizing the skin.

There exist devices for skin moisture measurement used for the assessment of skin condition. These devices can also be used for evaluating the efficacy of skin moisturizing products. Innumerable devices have been developed for the measurement of parameters sensitive to the moisture of skin. Some of the devices are expensive and complicated to use, but some are relatively cheap and easy to use, e.g. ohmmeters measuring the electric resistance of the skin. However, they have many shortcomings: the distance between the electrodes varies and the devices are sensitive to the electrolyte content of the intercellular space and to the skin contact.

The principle of the present moisture meters based on the measurement of the skin capacitance is that the skin is a capacitive part of a resonance circuit, either an RC-circuit or a monostabile multivibrator. A device containing an RC-circuit is introduced in the U.S. Pat. No. 4,860,753. A monostabile multivibrator is introduced in the U.S. Pat. No. 4,711,244. The skin causes a change in the resonance frequency of the circuit. The resonance frequency that indicates the properties of the skin is for instance calculated with a counter. One weakness of these devices is that the frequency of the measurement circuit depends on the properties of the skin. However, the dielectric properties of the skin change in relation to the frequency due to the influence of different types of dispersions. The dielectric properties determine the capacitance of the skin, which is the reason why a device measuring capacitance is not working reliably when its frequency changes. Another weakness of mentioned devices is that they are sensitive also to the resistivity of the skin, which means that, for example, the relative content of the electrolytes, which is independent of the water content of the stratum corneum, affects the measurement result.

The object of the present invention is to provide a method and an apparatus, which obviate the shortcomings of the present methods and apparatuses. It is a particular object of the invention to provide a method and an apparatus for measuring the moisture content of skin reliably, and that the resistivity of the skin does not affect the measurement result. It is a further object of the invention to provide an apparatus which is simple in its structure and economical to manufacture and to use.

In the method in accordance with the invention a wave signal is transmitted to the probe, the capacitance of the probe is measured by comparing the phases of the transmitted and reflected wave, and the applied radio frequency is low, approximately 0.2 to 5 MHz. This comparison can be performed with an appropriate device known as such.

This method enables accurate measurement of the capacitance of the probe even in the case when the conductance of the probe is much higher than the susceptance of the probe, which occurs always when the probe is in contact with the skin. In this arrangement the measurement result is independent of the conductance of the probe, which in practice means that the measurement result does not depend on the resistivity and further, for example, on the electrolyte content of the skin.

Operating frequency of the apparatus is an essential parameter of the method in accordance with the invention. The range used in the method is approximately 0.2 to 5 MHz. With lower frequencies than this, the susceptance of the probe decreases further and the difference between the conductance and the susceptance increases further. On the other hand, with frequencies higher than the specified range the measurement result contains information also from deeper layers of the skin. This is undesirable, because the water content of dermis does not affect what is commonly perceived as the moistness of the skin.

In an advantageous application of the invention the apparatus operates at only one frequency, the low radio frequency, approximately 0.2 to 5 MHz. When this method is used the apparatus operates only at one precisely set frequency, and thus gives a reliable result of the moisture content of skin. The capacitance of the skin is determined by its dielectric properties and therefore only such capacitance measuring apparatus which operates with a constant frequency, can be a reliable apparatus.

In a further advantageous application of the invention a wave signal is transmitted to the probe by an oscillator, and placing an attenuator on the signal path between the oscillator and the probe prohibits the reflections of the waves forming the signal between the oscillator and the probe. This means that the reflections do not affect the measurement result.

In a further application of the invention the phases of the wave transmitted to and reflected from the probe are deviated with a power splitter from each other by 90 degrees in addition to the minor phase difference caused by the probe. The resolution of the phase detector is then optimal and the accuracy of the measurement is better than when using a normal zero-degree power splitter.

In an additional application the phases of the wave transmitted to and reflected from the probe are compared by a phase detector. The phase detector is dependable and reliable but in other applications other devices can be used for this purpose.

Furthermore, in an advantageous additional application the propagating waves are amplified in the phase detector inputs so that the phase detector operates in a saturated state. Only then the phase detector or a similar device measures merely the phase shift of the incoming signals.

An apparatus in accordance with the invention comprises a device, preferably a phase detector, into the input of which the wave formed by the signal reflected from the probe is arranged to be led, and a wave forming the signal is arranged to be led into the other input of the device, then the capacitance can be measured by comparing the wave phases.

Figure 2:
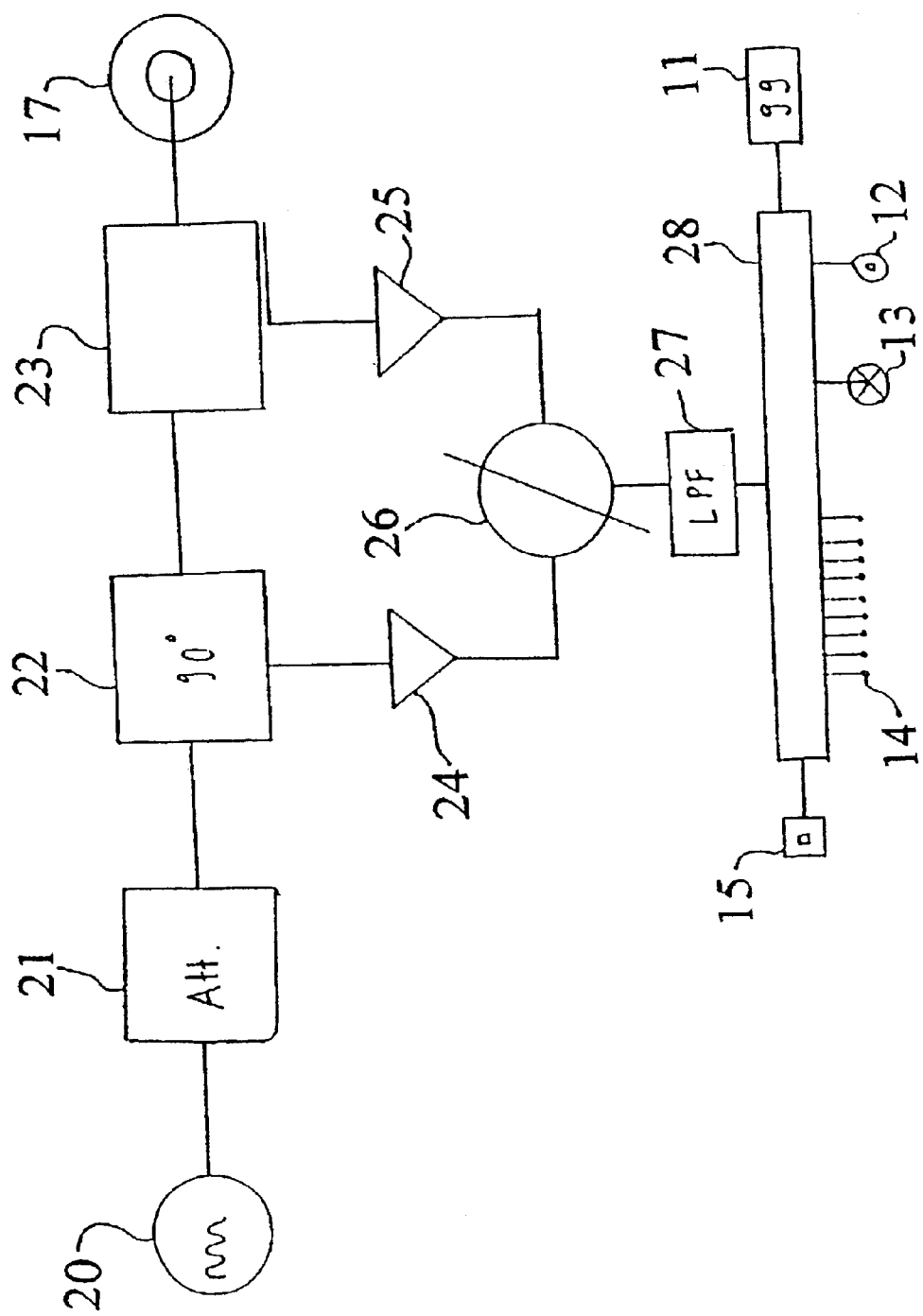
Figure 3:
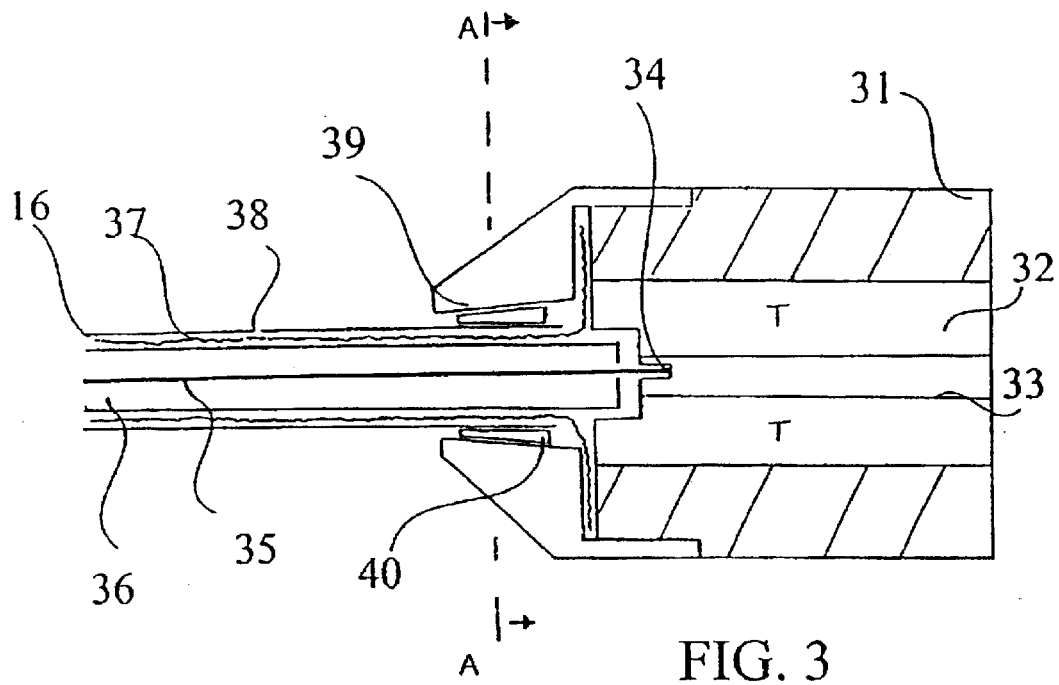
Figure 4:
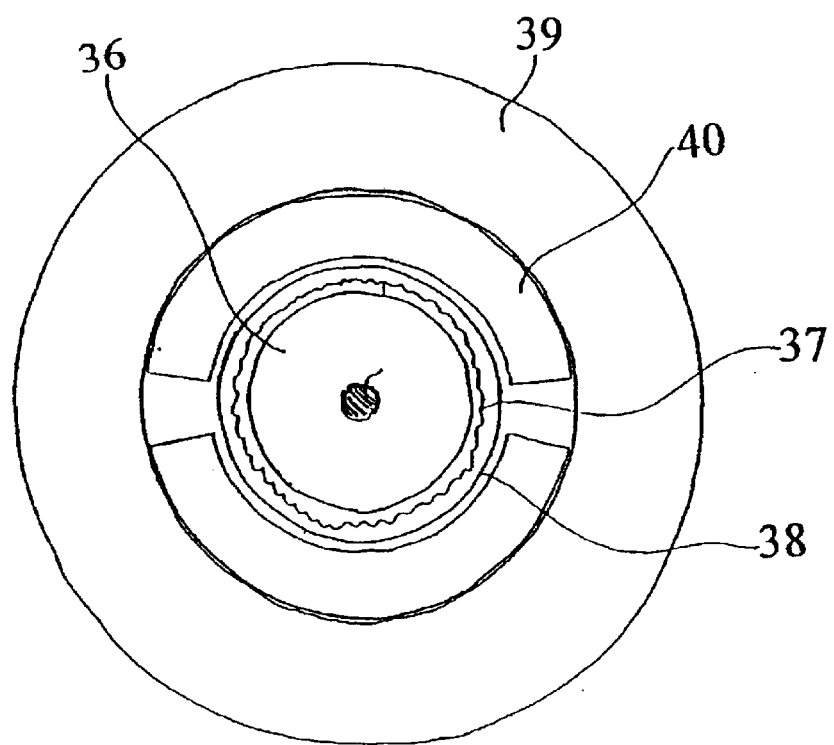

The invention will now be described in greater detail with reference to the accompanying drawings, where FIG. 1 shows the general view of an apparatus in accordance with the invention seen from above, FIG. 2 shows a block diagram showing the operation of the apparatus, FIG. 3 shows the longitudinal view of a probe, and FIG. 4 shows the cross-section A—A of FIG. 3.

FIG. 1 shows the case 10 of the apparatus and attached to it a display unit 11, a press button 12, an indicator light 13, a set of small LED lights 14 and a reset button 15. The shape of the case and the attached lights etc. can vary in different applications. From the case 10 outgoes a coaxial cable 16, in which a probe 17 is attached.

FIG. 2 shows an oscillator 20, an attenuator 21, a 90-degree power splitter 22, a directional coupler 23, two amplifiers 24 and 25, a probe 17, a phase detector 26, a low pass filter 27 and a digital electronic unit 28. A display unit 11, a press button 12, an indicator light 13, a set of LED lights 14 and a reset button 15 are connected to this electronic unit.

FIG. 3 shows a probe 17 comprising a brass-made outer electrode 31, a brass-made inner electrode 33 and a Teflon part 32. The inner electrode 33 is round and the ring-shaped outer electrode 31 surrounds it so that the Teflon part 32 is between them. The inner conductor 35 of the coaxial cable 16 is soldered in a small hole 34 on top of the inner electrode 33. Besides the inner conductor 35 the coaxial cable 16 comprises an outer conductor 37, dielectric material 36 between them and a sleeve 38. A separate clamping part 39 is pressed against the outer electrode 31 so that outer conductor 37 of the coaxial cable 16 is compressed between them, thus being in electric contact with the outer electrode 31. While the outer conductor 37 is pressed against the outer electrode 31, two wedge-like pieces 40 cause compression of the coaxial cable 16 against the clamping part 39. All parts in FIG. 3, apart from the wedge-like pieces 40, are rotationally symmetric.

FIG. 4 shows the cross section A—A of the probe similar to FIG. 3. The graph illustrates particularly the setting of the two wedge-like pieces 40.

The device is arranged to measure the phase coefficient of the probe's reflection coefficient at a single low radio frequency (which is approximately 0.2 to 5 MHz).

The radio frequency section of the apparatus, which comprises the parts 20–26 and the probe 17 in FIG. 2, is radio technically arranged. Practically this means that the lines between the components are microstrip lines with specific wave impedance, e.g. 50 ohm. Thus waves propagating in opposite directions can travel in the single signal path. In this context a signal means such a propagating wave. The operation of the high frequency components is not at all affected by the fact that the dimensions of the circuit are small compared with the wavelength.

The apparatus operates so that the outgoing sinusoidal signal from the oscillator 20 is led through the directional coupler 23 into the probe 17. The reflected signal from the probe 17 is connected to one input of the phase detector 26 through the directional coupler 23. A signal directly from the oscillator 20 through the power splitter 22 is led to the other input. The output of the phase detector 26 is proportional to the phase difference, which again is dependent only on the capacitance of the probe 17. Thus the apparatus operates with one single frequency, and the result is dependent only on the dielectric properties of the skin, not on conductivity.

The oscillator 20 of the apparatus is operating always when the apparatus is switched on. So there is a constant voltage in the output of the phase detector 26 and the subsequent low pass filter 27. The apparatus is used so that the press button 12 is pressed at the same time as the probe 17 is pressed on the skin. The measurement starts at this moment and the indicator light 13 is on during the measurement. The timer circuit in the digital electronic unit 28 activates the measurement for a preselected standard time, after which the indicator light 13 is switched off. The apparatus contains also a buzzer (not shown in the figures) inside the case 10 and it gives a sound indicating that the measurement is completed. After the measurement a reading appears at the display 11. The reading is proportional to the capacitance of the probe 17 and the moisture content of skin. The apparatus ends the measurement automatically when the measurement time is over and after that the reading shown at the display 11 is no longer affected by the skin contact of the probe 17. The LED indicators 14 operate completely in accordance with the display 11, thus the moisture content of skin can be read after the measurement merely by the amount of lights 14 switched on. The lights 14 have different colours: in case of dry skin only yellow lights are on, in case of normal skin besides yellow also green lights are on, and in case of moist skin besides the above mentioned lights also blue lights are on. Pressing the reset button 15 resets the display 11 and switches off the lights 14.

It is necessary to standardize the measurement time to obtain reliable measurement result, because the output voltage of the low pass filter 27 changes slowly but constantly when the probe 17 touches the skin. This is caused by the increase of moisture content of skin under the probe 17, when the skin contact of the probe 17 prevents the evaporation of the water vapour passing the skin. An appropriate measurement time is 5–20 seconds.

An essential feature of the radio frequency unit of the apparatus, containing the parts of the block diagram in FIG. 2 apart from the digital electronic unit 28, is that signal voltage in both inputs of the phase detector 26 is so high that the detector operates in a saturated state. Only then the phase detector 26 measures merely the phase shift of incoming signals. This phase shift is proportional to the capacitance of the probe 17, which again is proportional to the dielectric constant of the filling of the capacitor (in this case the surface of the skin). The dielectric constant depends on the moisture content of skin surface. Thus the measurement result is not affected e.g. by the electrolyte content, unlike in devices which are sensitive to the conductivity of the skin.

Another essential feature of the radio frequency unit is the attenuator 21 between the oscillator 20 and the power splitter 22. Its purpose is to prevent the reflected signal from the probe 17 from entering a wrong signal path, to the input of the amplifier 24. Due to the attenuator the reflected signal from the probe has to travel twice through the attenuator 21 when travelling to the input of the amplifier 24 after being reflected. If the attenuator 21 is e.g. 6 dB, the total attenuation with this signal is 12 dB, which is sufficient.

The present invention is not restricted to the described advantageous application, but it can be embodied in other forms within the limits of the inventional idea defined by the claims.

What is claimed is:

1. Method for measuring the moisture content of skin, including placing a probe on the skin for measuring the capacitance of the skin, transmitting a wave signal into the probe, measuring the capacitance of the probe by comparing the phases of the transmitted and reflected wave, wherein the moisture content of an uppermost layer of the skin is measured, and the applied radio frequency is approximately 0.2 to 5 MHz.

2. Method according to claim 1, wherein the apparatus operates only at one predetermined frequency.

3. Method according to claim 1 or 2, wherein the wave signal is transmitted to the probe from an oscillator and reflections of the waves forming the signal between the oscillator and the probe are prohibited by placing an attenuator on the signal path between the oscillator and the probe.

4. Method according to claim 1, wherein the phases of the wave transmitted to and reflected from the probe are deviated with a power splitter from each other by 90 degrees in addition to the minor phase difference caused by the probe.

5. Method according to claim 1, wherein the phases of the wave transmitted to and reflected from the probe are compared with a phase detector.

6. Method according to claim 5, wherein the waves are amplified in the phase detector inputs so that the phase detector operates in a saturated state.

7. Apparatus for measuring the moisture content of skin, comprising a probe to be placed on the skin and devices connected to the probe for transmitting and transferring a wave signal to the probe and for transferring and analyzing the signal reflected from the probe and for measuring the capacitance of the skin, wherein the apparatus contains a device, into which the wave formed by the signal reflected from the probe is arranged to be led into a first input, and into which a wave forming a signal and transmitted to the probe is arranged to be led into a second input, at which the capacitance can be measured by comparing the phases of the reflected and transmitted waves.

8. Apparatus according to claim 7, wherein the apparatus is arranged to operate only at one constant frequency.

9. Apparatus according to claim 7 or 8, further comprising an attenuator between an oscillator and a power splitter.

10. Apparatus according to claim 8, wherein the frequency is approximately 0.2 to 5 MHz.

11. Apparatus according to claim 7, wherein the device is a phase detector.

* * * * *